United States Patent [19]
Artz et al.

[11] Patent Number: 5,833,951
[45] Date of Patent: Nov. 10, 1998

[54] EMULSIFIER-FREE, FINELY DISPERSE COSMETIC OR DERMATOLOGICAL FORMULATIONS OF THE OIL-IN-WATER TYPE

[75] Inventors: Dorte Artz, Lüneburg; Michael Christiansen, Tornesch; Uwe Schönrock, Norderstedt; Sigrid Steinke, Hamburg, all of Germany

[73] Assignee: Beiersdorf AG, Hamburg, Germany

[21] Appl. No.: 776,137

[22] PCT Filed: Jul. 5, 1995

[86] PCT No.: PCT/EP95/02599
§ 371 Date: May 19, 1997
§ 102(e) Date: May 19, 1997

[87] PCT Pub. No.: WO96/02223
PCT Pub. Date: Feb. 1, 1996

[30] Foreign Application Priority Data

Jul. 16, 1994 [DE] Germany ............... 44 25 268.4

[51] Int. Cl.$^6$ .................... A61K 7/00
[52] U.S. Cl. .................... 424/47
[58] Field of Search .................... 424/47

*Primary Examiner*—Amelia Owens
*Attorney, Agent, or Firm*—Sprung Kramer Schaefer & Briscoe

[57] ABSTRACT

Finely disperse, emulsifier-free cosmetic or dermatological formulations of the oil-in-water type, comprising
- an oily phase comprising, as the main constituent, one or more non-polar oils, fats and/or waxes,
- an aqueous phase,
- one or more thickeners selected from the group consisting of acrylic polymers, polysaccharides and alkyl ethers thereof, these thickeners not being allowed to have emulsifier properties,
- and, if desired, comprising customary cosmetic or dermatological auxiliaries, additives and/or active compounds.

18 Claims, No Drawings

EMULSIFIER-FREE, FINELY DISPERSE COSMETIC OR DERMATOLOGICAL FORMULATIONS OF THE OIL-IN-WATER TYPE

BACKGROUND OF THE INVENTION

The present invention relates to cosmetic and dermatological formulations of the oil-in-water type, processes for their preparation and their use for cosmetic and medical purposes.

Cosmetic skin care is primarily to be understood as meaning that the natural function of the skin as a barrier against environmental influences (for example dirt, chemicals, microorganisms) and against the loss of endogenous substances (for example water, natural fats, electrolytes) is intensified or re-established.

If this function is impaired, an increased absorption of toxic or allergenic substances or attack by microorganisms and, as a consequence, toxic or allergic skin reactions may occur.

The aim of skin care is furthermore to compensate the loss of fats and water from the skin caused by daily washing. This is important precisely if the natural capacity for regeneration is inadequate. Skin care products should furthermore protect against environmental influences, in particular against sun and wind, and delay ageing of the skin.

As a rule, medical topical compositions comprise one or more medicaments in an active concentration. For simplicity, to make a clear distinction between cosmetic and medicinal use and corresponding products, reference is made to the legal provisions of the Federal Republic of Germany (for example cosmetics legislation and foodstuffs and medical preparations law).

In simple emulsions, one phase contains finely disperse droplets of the second phase enclosed by an emulsifier shell (water droplets in W/O emulsions or lipid vesicles in O/W emulsions).

The use of customary cosmetic emulsifiers is acceptable in itself. Nevertheless, emulsifiers, like any chemical substance in the end, can cause allergic reactions or reactions based on hypersensitivity of the user in an individual case.

It is thus known that certain photodermatoses can be triggered by certain emulsifiers, and also by various fats, and at the same time exposure to sunlight. Such photodermatoses are also called "Mallorca acne". One object of the present invention was therefore to develop emulsifier-free sunscreen products.

Emulsifier-free light protection preparations based on so-called hydrodispersions have been accessible to the consumer for some time.

Hydrodispersions are dispersions of a liquid, semi-solid or solid internal (discontinuous) lipid phase in an external aqueous (continuous) phase.

In contrast to O/W emulsions, which are distinguished by a similar phase arrangement, hydrodispersions are essentially free from emulsifiers. Hydrodispersions, like other emulsions otherwise, are metastable systems and tend to convert into a state of two discrete phases which are coherent in themselves. In emulsions, the choice of a suitable emulsifier prevents phase separation.

In hydrodispersions of a liquid lipid phase in an external aqueous phase, the stability of such a system can be guaranteed, for example, by building up in the aqueous phase a gel matrix in which the lipid droplets are suspended in a stable form.

Formulations of the prior art, however, in general have the disadvantage that they are either unstable, have a narrow range of use or are limited to a limited choice of starting substances. It is usually furthermore the case that compositions of the prior art contain little or even no skin care fats or oils.

An object of the present invention was to provide emulsifier-free finely disperse formulations of the oil-in-water type which do not have the disadvantages of the prior art. Another object of the invention was to enrich the limited range of emulsifier-free finely disperse formulations of the oil-in-water type of the prior art. It was furthermore an object of the present invention to provide stable, emulsifier-free formulations with a high fat and/or oil content.

SUMMARY OF THE INVENTION

Astonishingly, these objects are achieved by finely disperse, emulsifier-free cosmetic or dermatological formulations of the oil-in-water type comprising an oily phase comprising, as the main constituent, one or more non-polar oils, fats and/or waxes, an aqueous phase, one or more thickeners selected from the group consisting of acrylic polymers, polysaccharides and alkyl ethers thereof, these thickeners not being allowed to have emulsifier properties, and, if desired, comprising customary cosmetic or dermatological auxiliaries, additives and/or active compounds.

DETAILED DESCRIPTION OF THE INVENTION

A thickener advantageous in accordance with the invention is Carbomer 980, an acrylic acid polymer. Carbomer 980 is available, inter alia, under the trade name Synthalen M (Sigma).

It is true that EP-A 328 355 describes a finely dispersed cosmetic formulation of the oil-in-water type comprising 3–40% by weight of an oil phase, 0.02–2.0% by weight of an amphipathic emulsifier, and water. This amphipathic emulsifier can be chosen from the group consisting of acrylic acid polymers (termed Carbomers or Carbopols) having emulsifier properties, namely Carbopol 934, Carbopol 940, Carbopol 941, Carbopol 1342 and other amphipathic emulsifiers.

In accordance with the invention, however, the thickeners are acrylic acid polymers without emulsifier properties, for example Carbomer 980. In Seife-Öle-Fette Wachse 113, No. 5/1987, p.149 ff express reference is made to the fact that Carbomer 980, unlike the other abovementioned Carbomer and Carbopol grades, possesses no emulsifier properties whatsoever.

Therefore, the prior art was unable to point in the direction of the present invention.

Where the thickeners are polysaccharides and their alkyl ethers, it is advantageous to choose these from the group consisting of xanthan gum, methylcellulose, hydroxymethylcellulose, ethylcellulose, hydroxyethylcellulose, propylcellulose and hydroxypropylcellulose.

Appropriate cellulose derivatives are obtainable under the trade name Tylose (Hoechst).

It has been found favourable to choose at least one of the non-polar oils, fats and/or waxes from the group consisting of the microcrystalline waxes.

The non-polar fats, waxes and oils according to the invention are advantageously chosen from the group consisting of vaseline (petrolatum), paraffin oil and polyolefins. Among the polyolefins, polydecenes are the preferred substances.

It is furthermore possible and advantageous, although not absolutely necessary, to dispense with an additional content of silicone oils.

Formulations according to the invention advantageously comprise 0.5–50% by weight of one or more non-polar oils, 0.005–10% by weight of thickeners, if appropriate auxiliaries, additives or active compounds, and water.

Formulations according to the invention particularly advantageously comprise 0.5–50% by weight of petrolatum, 0.005–10% by weight of thickeners, if appropriate auxiliaries, additives or active compounds, and water.

Formulations according to the invention also particularly advantageously comprise 0.5–50% by weight of paraffin oil, 0.005–10% by weight of thickeners, if appropriate auxiliaries, additives or active compounds, and water.

Formulations according to the invention especially advantageously comprise 0.5–30% by weight of petrolatum, 0.5–30% by weight of paraffin oil, 0.005–10% by weight of thickeners, if appropriate auxiliaries, additives or active compounds, and water.

Formulations according to the invention preferably comprise 1.5–20% by weight of petrolatum, 3–18% by weight of paraffin oil, 0.1–2% by weight of thickeners, if appropriate auxiliaries, additives or active compounds, and water.

Formulations according to the invention particularly preferably comprise 5–10% by weight of petrolatum, 8–18% by weight of paraffin oil, 0.1–2% by weight of thickeners, if appropriate auxiliaries, additives or active compounds, and water.

Particularly advantageous formulations are furthermore obtained if antioxidants are employed as additives or active compounds. According to the invention, the formulations advantageously comprise one or more antioxidants. All the antioxidants suitable or customary for cosmetic and/or dermatological uses can be used as antioxidants which are favourable but nevertheless are to be used optionally.

The antioxidants are particularly advantageously chosen from the group consisting of amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal) chelators (for example α-hydroxy-fatty acids, palmitic acid, phytic acid or lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example gamma-linolenic acid, linoleic acid and oleic acid), folic acid and derivatives thereof, ubiquinone and ubiquinol and derivatives thereof, vitamin C and derivatives (for example ascorbyl palmitates, Mg ascorbyl phosphates and ascorbyl acetates), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives, which are suitable according to the invention (salts, esters, ethers, sugars, nucleotides, nucleosides, peptides and lipids), of these active compounds mentioned.

Oil-soluble antioxidants can be particularly advantageously employed in the context of the present invention.

An astonishing property of the present invention is that formulations according to the invention are very good vehicles for cosmetic or dermatological active compounds in the skin, preferred active compounds being antioxidants which can protect the skin against exposure to oxidation. Preferred antioxidants here are vitamin E and derivatives thereof and vitamin A and derivatives thereof.

The amount of antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof is/are the antioxidant or antioxidants, it is advantageous to choose the particular concentrations thereof from the range from 0.001 to 10% by weight, based on the total weight of the formulation.

If vitamin A or vitamin A derivatives or carotenes or derivatives thereof is/are the antioxidant or antioxidants, it is advantageous to choose the particular concentrations thereof from the range from 0.001 to 10% by weight, based on the total weight of the formulation.

It is of course known to the expert that high-quality cosmetic formulations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellents, alcohol, water, salts, substances having an antimicrobial, proteolytic or keratolytic action and the like.

Mutatis mutandis, corresponding requirements apply to the formulation of medicinal formulations.

Depending on their build-up, the formulations according to the invention can accordingly be used, for example, as skin protection cream, cleansing milk, sunscreen lotion, nutrient cream, vanishing cream or night cream and the like. Where appropriate, it is possible and advantageous to use the formulations according to the invention as a base for pharmaceutical formulations.

Those cosmetic and dermatological formulations which are in the form of a sunscreen agent are also favourable. These preferably additionally comprise at least one UVA filter substance and/or at least one UVB filter substance and/or at least one inorganic pigment, in addition to the active compound combinations according to the invention.

However, it is also advantageous in the context of the present inventions to compose those cosmetic and dermatological formulations of which the chief purpose is not protection from sunlight but which nevertheless comprise a content of UV protection substances. Thus, for example, UV-A or UV-B filter substances are usually incorporated into vanishing creams.

UV protection substances, like antioxidants and, if desired, preservatives, also represent active protection of the formulations themselves against decay.

Formulations according to the invention can advantageously comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic and/or dermatological formulations which protect the skin from the entire range of ultraviolet radiation. They can also be used as sunscreen agents.

The UVB filters can be oil-soluble or water-soluble. Oil-soluble substances which may be mentioned are, for example:

- 3-benzylidenecamphor derivatives, preferably 3-(4-methylbenzylidene)camphor and 3-benzylidenecamphor;
- 4-aminobenzoic acid derivatives, preferably 2-ethylhexyl 4-(dimethylamino)benzoate and amyl 4-(dimethylamino)benzoate;
- esters of cinnamic acid, preferably 2-ethylhexyl 4-methoxycinnamate and isopentyl 4-methoxycinnamate;
- esters of salicylic acid, preferably 2-ethylhexyl salicylate, 4-isopropylbenzyl salicylate and homomenthyl salicylate;
- derivatives of benzophenone, preferably 2-hydroxy-4-methoxybenzophenone, 2-hydroxy-4-methoxy-4'-methylbenzophenone and 2,2'-dihydroxy-4-methoxybenzophenone;
- esters of benzalmalonic acid, preferably di (2-ethylhexyl) 4-methoxybenzalmalonate;
- 2,4,6-trianilino-(p-carbo-2'-ethyl-1'-hexyloxy)-1,3,5-triazine.

Advantageous water-soluble substances are:
- salts of 2-phenylbenzimidazole-5-sulphonic acid, such as its sodium, potassium or its triethanolammonium salt, and sulphonic acid itself;
- sulphonic acid derivatives of benzophenones, preferably 2-hydroxy-4-methoxybenzophenone-5-sulphonic acid and its salts;
- sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and their salts.

The list of UVB filters mentioned, which can be used according to the invention, is of course not intended to be limiting.

The invention also relates to the combination of a UVA filter according to the invention with a UVB filter, and to a cosmetic or dermatological formulation according to the invention which includes a UVB filter.

It may also be advantageous in formulations according to the invention to employ UVA filters which are customarily present in cosmetic and/or dermatological formulations. Substances of this kind are preferably derivatives of dibenzoylmethane, especially 1-(4'-tertbutylphenyl)-3-(4'-methoxyphenyl)propane-1,3-dione and 1-phenyl-3(4'-isopropylphenyl)propane-1,3-dione. Formulations comprising these combinations are also a subject of the invention. It is possible to use the same amounts of UVA filter substances as were mentioned for UVB filter substances.

Cosmetic and/or dermatological formulations according to the invention can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide. The amounts mentioned for the above combinations may be used.

The cosmetic and dermatological formulations according to the invention can comprise cosmetic auxiliaries such as are usually used in such formulations, for example preservatives, bactericides, virucides, perfumes, substances for preventing foaming, dyes, pigments which have a colouring action, thickening agents, surface-active substances, emulsifiers, softening, moistening and/or humectant substances, anti-inflammatory substances, medicaments, fats, oils, waxes or other customary constituents of a cosmetic or dermatological formulation, such as alcohols, polyols, polymers, foam stabilizers, electrolytes or organic solvents.

Further constituents which can be used are:

- fats, waxes and other natural and synthetic fat substances, preferably esters of fatty acids with alcohols of low C number, for example with isopropanol, propylene glycol or glycerol, or esters of fatty alcohols with alkanoic acids of low C number or with fatty acids;
- alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent. The following examples are intended to illustrate the present invention.

| Example 1 | | % by weight |
|---|---|---|
| (a) | | |
| Vaseline (Witco) | | 9.00 |
| Liquid paraffin | | 18.00 |
| $C_{12-15}$-alcohol benzoate (Finsolv TN, Erbslö) | | 3.00 |
| Carbomer 980 (Synthalen M, Sigma) | | 1.70 |
| (b) | | |
| Ethanol | | 5.00 |
| (c) | | |
| Butylene glycol | | 5.00 |
| NaOH (45%) | | 1.20 |
| Water | to | 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

| Example 2 | % by weight |
|---|---|
| (a) | |
| Vaseline (Witco) | 6.00 |
| Polydecene (Nexbase, Nynas) | 16.00 |
| $C_{12-15}$-alcohol benzoate (Finsolv TN, Erbslö) | 2.00 |
| Carbopol 980 (Goodrich) | 0.80 |
| (b) | |
| Preservative | q.s |
| (c) | |
| Propylene glycol | 4.00 |
| Glycerol | 3.00 |
| NaOH (45%) | 0.70 |
| Water | to 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

| Example 3 | % by weight |
|---|---|
| (a) | |
| Vaseline (Witco) | 5.00 |
| Liquid paraffin | 14.00 |
| Carbopol 980 (Goodrich) | 0.40 |
| (b) | |
| Ethanol | 10.00 |
| (c) | |
| Butylene glycol | 5.00 |
| NaOH (45%) | 0.35 |
| Water | to 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

| Example 4 | % by weight |
|---|---|
| (a) | |
| Vaseline (Witco) | 9.00 |
| Liquid paraffin | 18.00 |
| $C_{12-15}$-alcohol benzoate (Finsolv TN, Erbslö) | 3.00 |
| Carbomer 980 (Synthalen M, Sigma) | 1.70 |
| α-Tocopheryl acetate | 1.00 |
| (b) | |
| Ethanol | 5.00 |
| (c) | |
| Butylene glycol | 5.00 |
| NaOH (45%) | 1.20 |
| Water | to 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

| Example 5 | % by weight |
|---|---|
| (a) | |
| Vaseline (Witco) | 6.00 |
| Polydecene (Nexbase, Nynas) | 16.00 |
| $C_{12-15}$-alcohol benzoate (Finsolv TN, Erbslö) | 2.00 |
| Carbopol 980 (Goodrich) | 0.80 |
| Octyl methoxycinnamate | 2.00 |
| Parsol ® 1789 | 0.20 |
| (b) | |
| Preservative | q.s. |
| (c) | |
| Propylene glycol | 4.00 |
| Glycerol | 3.00 |
| NaOH (45%) | 0.70 |
| Water | to 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

| Example 6 | % by weight |
|---|---|
| (a) | |
| Vaseline (Witco) | 5.00 |
| Liquid paraffin | 14.00 |
| Carbopol 980 (Goodrich) | 0.40 |
| α-Tocopheryl acetate | 1.00 |
| Octyl methoxycinnamate | 2.00 |
| Parsol ® 1789 | 0.20 |
| (b) | |
| Ethanol | 10.00 |
| (c) | |
| Butylene glycol | 5.00 |
| NaOH (45%) | 0.35 |
| Water | to 100.00 |

Preparation: Phases (a) and (c) are heated separately to 75° C. Then phases (a) and (c) are combined and cooled with stirring to about 65° C. The mixture is then homogenized and cooled with stirring to about 35° C. Phase (b) is added, then homogenization is carried out again and the mixture is cooled to room temperature.

We claim:

1. Finely disperse, emulsifier-free cosmetic or dermatological formulations of the oil-in-water type, comprising
   an oily phase comprising, as the main constituent, one or more non-polar oils, fats and/or waxes,
   an aqueous phase,
   one or more thickeners selected from the group consisting of acrylic polymers, polysaccharides and alkyl ethers thereof, these thickeners not being allowed to have emulsifier properties,
   and, optionally, comprising customary cosmetic or dermatological auxiliaries, additives and/or active compounds.

2. Formulations according to claim 1, wherein the oils, fats and waxes are chosen from the group consisting of vaseline, paraffin oil and polyolefins.

3. Formulations according to claim 1, wherein the thickener or thickeners is or are chosen from the group consisting of xanthan gum, methylcellulose, hydroxymethylcellulose, ethylcellulose, hydroxyethylcellulose, propylcellulose, and hydroxypropylcellulose.

4. Formulations according to claim 1, wherein the acrylic polymer or polymers is or are chosen from the group of the Carbopols which possess no emulsifier properties.

5. Formulations according to claim 1, comprising 0.5–50% by weight of one or more non-polar oils, 0.005–10% by weight of thickeners, optionally auxiliaries, additives or active compounds, and water.

6. Formulations according to claim 1, comprising 1.5–20% by weight of petrolatum, 3–18% by weight of paraffin oil, 0.1–2% by weight of thickeners, optionally auxiliaries, additives or active compounds, and water.

7. Formulations according to claim 1, comprising 5–10% by weight of petrolatum, 8–18% by weight of paraffin oil, 0.1–2% by weight of thickeners, optionally auxiliaries, additives or active compounds, and water.

8. Formulations according to claim 1, comprising one or more additives or active compounds selected from the group consisting of antioxidants and UV protection agents.

9. In a method for transporting an active compound into the skin, the improvement which comprises employing a formulation of claim 1 as cosmetic or dermatological vehicle to transport the active compound.

10. The method according to claim 9 wherein the active compound is an antioxidant.

11. Formulations according to claim 1, wherein the formulations contain no emulsifiers.

12. Formulations according to claim 2, wherein the formulations contain no emulsifiers.

13. Formulations according to claim 3, wherein the formulations contain no emulsifiers.

14. Formulations according to claim 4, wherein the formulations contain no emulsifiers.

15. Formulations according to claim 5, wherein the formulations contain no emulsifiers.

16. Formulations according to claim 6, wherein the formulations contain no emulsifiers.

17. Formulations according to claim 7, wherein the formulations contain no emulsifiers.

18. Formulations according to claim 8, wherein the formulations contain no emulsifiers.

* * * * *

UNITED STATES PATENT AND TRADEMARK OFFICE
CERTIFICATE OF CORRECTION

PATENT NO : 5,833,951
DATED : November 10, 1998
INVENTOR(S): Dorte ARTZ, et al.

It is certified that error appears in the above-identified patent and that said Letters Patent is hereby corrected as shown below:

Title Page [54] "Title" and Col. 1     Delete "EMULSIFIER FREE, FINELY DISPERSE COSMETIC OR DERMATOLOGICAL FORMULATIONS OF THE OIL-IN-WATER TYPE" and substitute --EMULSIFIER-FREE, FINELY DISPERSED COSMETIC OR DERMATOLOGICAL OIL-IN-WATER TYPE PREPARATIONS--

Title Page, "Inventors"     After "Schonrock" delete "Norderstedt" and insert --Nahe--

Signed and Sealed this

Second Day of May, 2000

*Attest:*

Q. TODD DICKINSON

*Attesting Officer*     *Director of Patents and Trademarks*